US007060644B2

(12) United States Patent
Ghosh et al.

(10) Patent No.: US 7,060,644 B2
(45) Date of Patent: Jun. 13, 2006

(54) AROMATIC ALKYLATION CATALYST AND METHOD

(75) Inventors: Ashim Kumar Ghosh, Houston, TX (US); Gopalakrishnan Juttu, Sugar Land, TX (US); Pamela Harvey, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 0 days.

(21) Appl. No.: 10/753,742

(22) Filed: Jan. 8, 2004

(65) Prior Publication Data

US 2005/0154242 A1    Jul. 14, 2005

(51) Int. Cl.
*B01J 29/06* (2006.01)
*B01J 29/18* (2006.01)
*B01J 29/40* (2006.01)

(52) U.S. Cl. .............................. 502/60; 502/74; 502/77; 502/78

(58) Field of Classification Search ................. 502/60, 502/74, 77, 78, 75
See application file for complete search history.

(56) References Cited

U.S. PATENT DOCUMENTS

| 3,562,345 A | * | 2/1971 | Mitsche ..................... 585/475 |
| 4,025,606 A | * | 5/1977 | Acres ...................... 423/245.3 |
| 4,548,914 A | | 10/1985 | Chu |
| 4,590,321 A | | 5/1986 | Chu |
| 4,623,530 A | | 11/1986 | Cullo et al. |
| 4,623,533 A | | 11/1986 | Broecker et al. |
| 4,638,106 A | | 1/1987 | Pieters et al. |
| 4,665,251 A | | 5/1987 | Chu |
| 4,670,616 A | | 6/1987 | De Simone et al. |
| 4,673,767 A | | 6/1987 | Nimry et al. |
| 4,694,114 A | | 9/1987 | Chu et al. |
| 4,695,666 A | | 9/1987 | Chao et al. |
| 4,695,667 A | | 9/1987 | Sumitani et al. |
| 4,704,495 A | | 11/1987 | Dessau |
| 4,716,135 A | | 12/1987 | Chen |
| 4,721,827 A | | 1/1988 | Cullo et al. |
| 4,727,209 A | | 2/1988 | Chao |
| 4,746,763 A | | 5/1988 | Kocal |
| 4,758,328 A | | 7/1988 | Young |
| 4,761,513 A | | 8/1988 | Steacy |

(Continued)

OTHER PUBLICATIONS

F.M. Bautista, et al., Continuous Flow Toluene Methylation Over AlPO4 and AlPO4-Al2O3 Catalysts, Catalysis Letters, 1994, pp. 159-167, vol. 26, no month.

(Continued)

*Primary Examiner*—Elizabeth D. Wood
(74) *Attorney, Agent, or Firm*—Grady K. Bergen; Jim D. Wheelington

(57) ABSTRACT

A catalyst for use in aromatic alkylation, such as toluene alkylation with methanol, is comprised of a zeolite with pore size from about 5.0 to about 7.0 Å containing a hydrogenating metal. The catalyst may be used in preparing an alkyl aromatic product by providing the catalyst within a reactor. The catalyst may be contacted with an aromatic hydrocarbon and an alkylating agent in the presence of hydrogen under reaction conditions suitable for aromatic alkylation. The catalyst may also be treated to further increase its stability. This is accomplished by heating the hydrogenating metal loaded zeolite catalyst in the presence of a reducing agent prior to use in an aromatic alkylation reaction to a temperature of from about 400° C. to about 500 ° C. for about 0.5 to about 10 hours.

17 Claims, 4 Drawing Sheets

U.S. PATENT DOCUMENTS

| | | | |
|---|---|---|---|
| 4,847,223 A | 7/1989 | Le Van Mao et al. |
| 4,861,930 A | 8/1989 | Cottrell et al. |
| 4,873,067 A | 10/1989 | Valyocsik et al. |
| 4,891,197 A | 1/1990 | Derouane et al. |
| 4,891,467 A | 1/1990 | Sikkenga |
| 4,902,406 A | 2/1990 | Valyocsik |
| 4,912,073 A | 3/1990 | Chu |
| 4,914,067 A | 4/1990 | Pellet et al. |
| 4,935,574 A | 6/1990 | D'Amore et al. |
| 4,962,255 A | 10/1990 | Fraenkel et al. |
| 4,973,781 A | 11/1990 | Valyocsik et al. |
| 5,041,402 A | 8/1991 | Casci et al. |
| 5,043,502 A | 8/1991 | Martindale et al. |
| 5,047,141 A | 9/1991 | Chu |
| 5,068,483 A | 11/1991 | Barthomeuf et al. |
| 5,094,995 A | 3/1992 | Butt et al. |
| 5,105,047 A | 4/1992 | Waller |
| 5,108,579 A | 4/1992 | Casci |
| 5,110,776 A | 5/1992 | Chitnis et al. |
| 5,124,299 A | 6/1992 | Waller |
| 5,171,921 A | 12/1992 | Gaffney et al. |
| 5,173,461 A | 12/1992 | Absil et al. |
| 5,178,748 A | 1/1993 | Casci et al. |
| 5,231,064 A | 7/1993 | Absil et al. |
| 5,233,102 A | 8/1993 | Butt et al. |
| 5,246,688 A | 9/1993 | Faust et al. |
| 5,248,841 A | 9/1993 | Young |
| 5,254,767 A | 10/1993 | Dwyer |
| 5,254,770 A | 10/1993 | Olson et al. |
| 5,294,578 A | 3/1994 | Ho et al. |
| 5,315,033 A | 5/1994 | Butt et al. |
| 5,318,696 A | 6/1994 | Kowalski |
| 5,321,183 A | 6/1994 | Chang et al. |
| 5,330,732 A * | 7/1994 | Ishibashi et al. ......... 423/213.2 |
| 5,336,478 A | 8/1994 | Dwyer et al. |
| 5,345,021 A | 9/1994 | Casci et al. |
| 5,348,643 A | 9/1994 | Absil et al. |
| 5,349,113 A | 9/1994 | Chang et al. |
| 5,365,003 A | 11/1994 | Chang et al. |
| 5,366,948 A | 11/1994 | Absil et al. |
| 5,367,100 A | 11/1994 | Gongwei et al. |
| 5,371,307 A | 12/1994 | Guth et al. |
| 5,378,670 A | 1/1995 | Kumar |
| 5,380,690 A | 1/1995 | Zhicheng et al. |
| 5,385,718 A | 1/1995 | Casci et al. |
| 5,399,336 A | 3/1995 | Guth et al. |
| 5,430,212 A | 7/1995 | Butt et al. |
| 5,430,213 A | 7/1995 | Hendriksen et al. |
| 5,446,234 A | 8/1995 | Casci et al. |
| 5,455,213 A | 10/1995 | Chang et al. |
| 5,456,821 A | 10/1995 | Absil et al. |
| 5,464,799 A | 11/1995 | Casci et al. |
| 5,475,179 A | 12/1995 | Chang et al. |
| 5,498,814 A | 3/1996 | Chang et al. |
| 5,503,818 A | 4/1996 | Nicolaides |
| 5,512,260 A | 4/1996 | Kiliany et al. |
| 5,516,736 A | 5/1996 | Chang et al. |
| 5,523,510 A | 6/1996 | Pellet et al. |
| 5,529,964 A * | 6/1996 | Weitkamp et al. ............ 502/74 |
| 5,534,239 A | 7/1996 | Fajula et al. |
| 5,536,894 A | 7/1996 | Degnan et al. |
| 5,541,146 A | 7/1996 | Chang et al. |
| 5,561,095 A | 10/1996 | Chen et al. |
| 5,563,310 A | 10/1996 | Chang et al. |
| 5,569,805 A | 10/1996 | Beck et al. |
| 5,571,768 A | 11/1996 | Chang et al. |
| 5,573,746 A | 11/1996 | Chen |
| 5,576,256 A | 11/1996 | Monque et al. |
| 5,607,888 A | 3/1997 | Chang et al. |
| 5,607,890 A | 3/1997 | Chen et al. |
| 5,646,314 A | 7/1997 | Crocco et al. |
| 5,648,580 A | 7/1997 | Chen et al. |
| 5,658,454 A | 8/1997 | Absil et al. |
| 5,675,047 A | 10/1997 | Beck et al. |
| 5,689,024 A | 11/1997 | Schmitt |
| 5,698,756 A | 12/1997 | Beck et al. |
| 5,780,563 A | 7/1998 | Chen et al. |
| 5,789,335 A | 8/1998 | Chen et al. |
| 5,811,613 A | 9/1998 | Bhat et al. |
| 5,833,840 A | 11/1998 | Absil et al. |
| 5,902,919 A | 5/1999 | Chen et al. |
| 5,905,051 A | 5/1999 | Wu et al. |
| 5,922,922 A | 7/1999 | Harris et al. |
| 5,925,586 A | 7/1999 | Sun |
| 5,939,597 A | 8/1999 | Dessau et al. |
| 5,951,963 A | 9/1999 | He et al. |
| 5,955,641 A | 9/1999 | Chen et al. |
| 5,968,463 A * | 10/1999 | Shelef et al. ............ 423/213.5 |
| 5,994,603 A | 11/1999 | Mohr et al. |
| 6,034,283 A | 3/2000 | Ban et al. |
| 6,040,257 A | 3/2000 | Drake et al. |
| 6,040,259 A * | 3/2000 | Mohr et al. ................... 502/67 |
| 6,046,128 A | 4/2000 | Kisen et al. |
| 6,047,544 A | 4/2000 | Yamamoto et al. |
| 6,048,816 A | 4/2000 | Brown et al. |
| 6,060,633 A | 5/2000 | Chen et al. |
| 6,074,975 A | 6/2000 | Yao et al. |
| 6,080,303 A | 6/2000 | Cao et al. |
| 6,080,698 A | 6/2000 | Zhang et al. |
| 6,083,865 A | 7/2000 | Drake et al. |
| 6,090,274 A | 7/2000 | Wu et al. |
| 6,100,437 A | 8/2000 | Koehl et al. |
| 6,124,227 A | 9/2000 | Yao et al. |
| 6,150,293 A | 11/2000 | Verduijn et al. |
| 6,156,949 A | 12/2000 | Brown et al. |
| 6,160,191 A | 12/2000 | Smith et al. |
| 6,187,982 B1 | 2/2001 | Beck et al. |
| 6,211,104 B1 | 4/2001 | Shi et al. |
| 6,217,748 B1 | 4/2001 | Hatanaka et al. |
| 6,251,263 B1 | 6/2001 | Hatanaka et al. |
| 6,294,493 B1 | 9/2001 | Strohmaier et al. |
| 6,299,530 B1 | 10/2001 | Chen et al. |
| 6,300,535 B1 | 10/2001 | van den Berge et al. |
| 6,306,790 B1 | 10/2001 | Rodriguez et al. |
| 6,319,484 B1 * | 11/2001 | Shore et al. ............ 423/245.1 |
| 6,342,153 B1 | 1/2002 | Guan et al. |
| 6,388,156 B1 | 5/2002 | Ou et al. |
| 6,395,664 B1 | 5/2002 | Boehner et al. |
| 6,417,421 B1 | 7/2002 | Yao |
| 6,423,879 B1 | 7/2002 | Brown et al. |
| 6,444,610 B1 | 9/2002 | Yamamoto |
| 6,459,006 B1 | 10/2002 | Ou et al. |
| 6,469,095 B1 | 10/2002 | Gareiss et al. |
| 6,503,862 B1 | 1/2003 | Yamamoto |
| 6,504,072 B1 | 1/2003 | Brown et al. |
| 6,504,074 B1 | 1/2003 | Verduijn et al. |
| 6,506,954 B1 | 1/2003 | Brown et al. |
| 6,518,213 B1 | 2/2003 | Yamamoto et al. |
| 6,548,725 B1 | 4/2003 | Froment et al. |
| 6,566,293 B1 | 5/2003 | Vogt et al. |
| 6,589,901 B1 | 7/2003 | Yamamoto |
| 6,613,708 B1 | 9/2003 | Ou et al. |
| 6,613,951 B1 | 9/2003 | Brown et al. |
| 6,642,426 B1 | 11/2003 | Johnson et al. |
| 6,689,929 B1 | 2/2004 | Williams et al. |
| 6,699,811 B1 | 3/2004 | Mohr et al. |
| 6,723,297 B1 | 4/2004 | Chen et al. |
| 6,726,834 B1 | 4/2004 | Quesada et al. |
| 6,770,251 B1 | 8/2004 | Yoshikawa |
| 6,773,694 B1 | 8/2004 | Lesch et al. |
| 6,799,089 B1 | 9/2004 | Toulhoat |
| 6,811,684 B1 | 11/2004 | Mohr et al. |
| 6,812,181 B1 | 11/2004 | van der Berge et al. |

OTHER PUBLICATIONS

Oyvind Kikkelson, et al., Use of Isotopic Labeling for Mechanistic Studies of the Methanol-to-Hydrocarbons reaction. Methylation of toluene with Methanol Over H-ZSM-5, H-Mordenite and H-Beta, Microporous and Mesoporous Materials, 2000, pp. 93-113, vol. 40, no month.

P.G. Smirniotis, et al., Alkylation of Benzene or Toluene with MeOH or C2H4 over ZSM-5 or B-Zeolite: Effect of the Zeolite Pore Openings and of the Hydrocarbons Involved on the Mechanism of Alkylation, Ind. Eng. Chem. Res., 1995, pp. 1517-1528, vol. 34, no month.

F.M. Bautista, et al., Continuous Flow Toluene Methylation Over AlPO4 and AlPO4-Al2O3 Catalysts, Catalysis Letters, 1994, pp. 159-167, vol. 26, no month.

* cited by examiner

AROMATIC ALKYLATION CATALYST AND METHOD

TECHNICAL FIELD

The invention relates generally to the alkylation of aromatic compounds and catalysts used for such reactions.

BACKGROUND

Para-xylene is a valuable substituted aromatic compound because of its great demand for its oxidation to terephthalic acid, a major component in forming polyester fibers and resins. It can be commercially produced from hydrotreating of naphtha (catalytic reforming), steam cracking of naphtha or gas oil, and toluene disproportionation.

Alkylation of toluene with methanol, which is also known as toluene methylation, has been used in laboratory studies to produce para-xylene. Toluene methylation has been known to occur over acidic catalyst, particularly over zeolite or zeolite-type catalyst. In particular, ZSM-5-type zeolite, zeolite Beta and silicaaluminophosphate (SAPO) catalysts have been used for this process. Generally, a thermodynamic equilibrium mixture of ortho (o)-, meta (m)- and para (p)-xylenes can be formed from the methylation of toluene, as is illustrated by the reaction below.

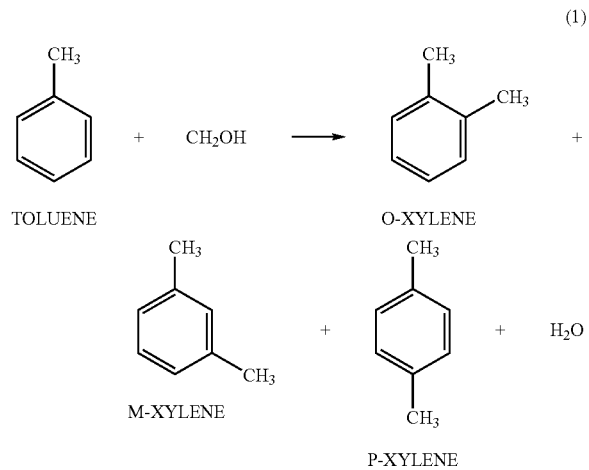

Thermodynamic equilibrium compositions of o-, m-, and p-xylenes may be around 25, 50 and 25 mole %, respectively, at a reaction temperature of about 500° C. Such toluene methylation may occur over a wide range of temperatures, however. Para-xylene can be separated from mixed xylenes by a cycle of adsorption and isomerization. Byproducts such as C9+ and other aromatic products can be produced by secondary alkylation of the xylene product.

A significantly higher amount of p-xylene can be obtained in toluene methylation reaction if the catalyst has shape selective properties. Shape selective properties can be obtained in modified zeolite catalysts by narrowing zeolite pore opening size, inactivation of the external surface of the zeolite or controlling zeolite acidity. Toluene methylation may occur over modified ZSM-5 or ZSM-5-type zeolite catalyst giving xylene products containing significantly greater amounts of p-xylene than the thermodynamic concentration.

Unfortunately, there are a number of technical hurdles for toluene methylation to be commercially successful. These include fast catalyst deactivation, low methanol selectivity, and so on. Most of the catalysts, if not all, for toluene methylation show fast catalyst deactivation. Typically, toluene conversion declines with time on stream due to rapid coke formation on the catalyst. The catalyst deactivation is one of the most difficult technical hurdles to overcome for commercial use of toluene methylation.

The present invention describes a catalyst and a method for its activation for catalyst stability for toluene methylation. The catalyst described here produces mixed xylene with isomers of thermodynamic concentrations from toluene methylation reaction, and the catalyst shows improved stability for toluene conversion. The invention has application to other aromatic alkylation reactions, as well.

BRIEF DESCRIPTION OF THE DRAWINGS

For a more complete understanding of the present invention, reference is now made to the following descriptions taken in conjunction with the accompanying figures, in which.

DETAILED DESCRIPTION

Figure 1:
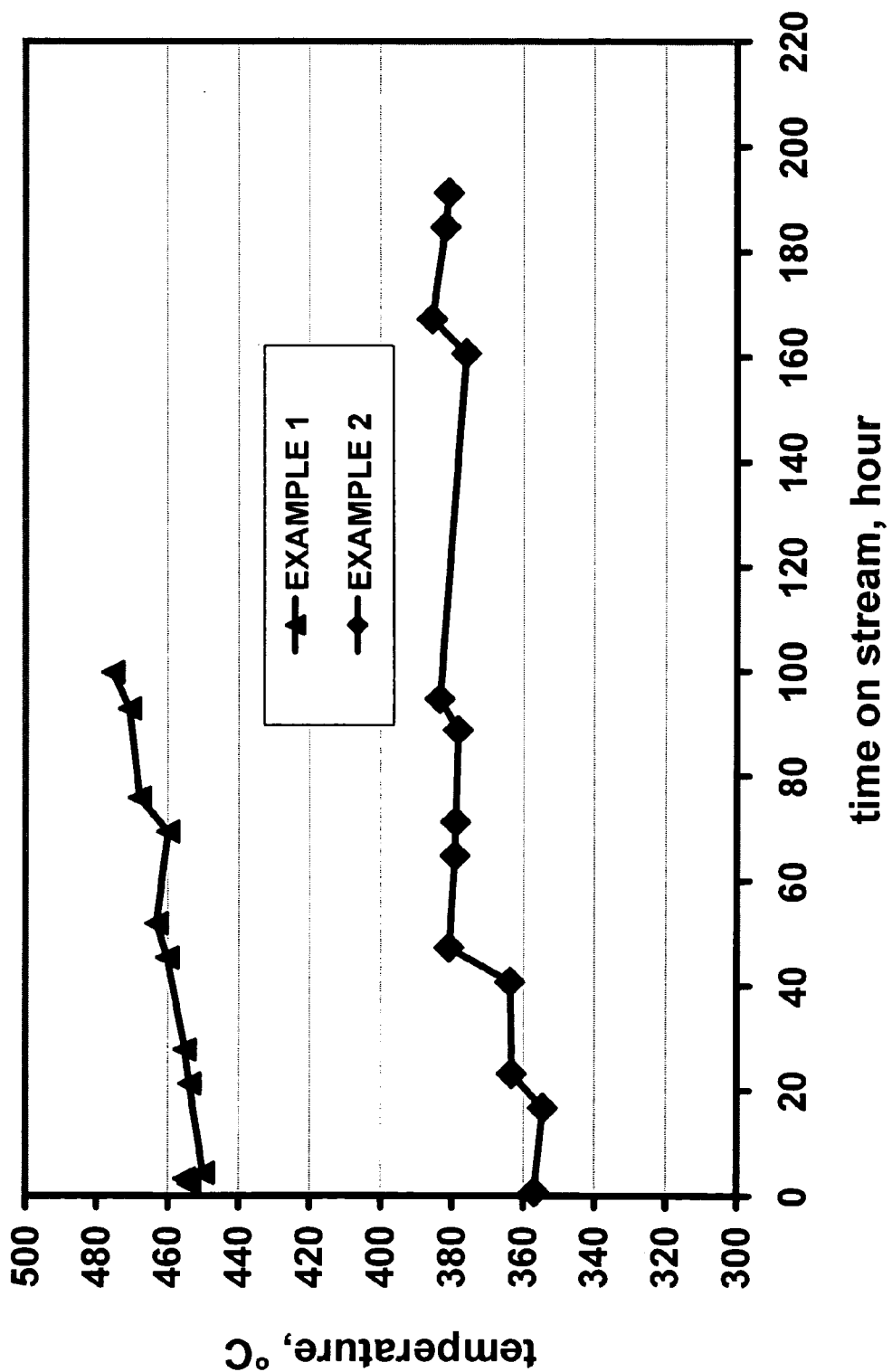
FIG. 1 is a plot of reactor temperature to achieve constant conversion over time for the toluene methylation reaction of Examples 1 and 2.

It has been found that by combining a hydrogenating-metal, such as nickel, with a zeolite catalyst that is useful in aromatic alkylation reactions, and which may be pretreated prior to feed introduction, deactivation of the catalyst can be significantly reduced. Such aromatic alkylation reactions may include toluene alkylation with an alkylating agent such as methanol, light alkane or their combinations. Such zeolite catalysts are typically acid catalysts having a $SiO_2/Al_2O_3$ molar ratio of from about 10 to about 1000. In particular, the zeolite catalysts may have a pore size of from about 5.0 Å to about 7.0 Å. The zeolite may include ZSM-5 zeolites, Omega or mordenite.

The hydrogenating metal may be any of the group VIIIA transition metals and may include nickel, palladium and platinum, as well as other metals. The hydrogenating metal may be present in an amount of from about 0.1 to about 5.0 wt %, more particularly, from about 0.2 to about 3.0 wt % of the zeolite catalyst. The hydrogenating metal may be combined with the zeolite catalyst by impregnating the catalyst with the hydrogenating metal by a wet incipient method using compounds containing the desired hydrogenating metal, or by an ion-exchange technique using a hydrogenating-metal salt. The impregnation or ion-exchange techniques for combining the metal in the zeolite catalyst are well known in the art.

The catalyst may be a bound or unbound catalyst. Suitable binders may include alumina, clay, and silica. Techniques used for preparing the bound catalyst are well known in the art. The catalyst, bound or unbound, may be calcined at a temperature between 400° C. and 570° C. in an environment containing oxygen, typically air. The hydrogenating metal in the catalyst after such calcinations may be present in the oxide form, for example, Ni as NiO. Also, $NH_4$-ZSM-5 will transform to HZSM-5 after calcinations.

The hydrogenating metal loaded zeolite catalyst may be further pretreated prior to use in alkylation reactions to reduce or to lower oxidation state of the hydrogenating metal in a reducing environment. Such treatment includes contacting the catalyst with a reducing gas at an elevated temperature. The reducing gas may be hydrogen ($H_2$) or hydrogen-containing gas such as a mixture of hydrogen and nitrogen ($N_2$) or light alkane(s). The catalyst is contacted with the reducing gas, which may be mixed with an inert carrier gas, such as nitrogen at an initial starting temperature. The temperature may be slowly ramped up during the pretreatment, with the initial starting temperature being from about 100 to about 200° C., and which is increased at a rate of from about 0.2 to about 10.0° C./min to the final pretreatment temperature. The final pretreatment temperature may be from about 400 to about 500° C., more particularly from about 410 to about 450° C. The pretreatment may be carried out from about 0.5 to 10 hours or more, more particularly from 1 to 9 hours, and still more particularly from about 2 to 7 hours.

Based on temperature programmed reduction profile data on NiO or the $Ni^{2+}$ containing zeolite catalyst, it is believed that the above described catalyst pretreatment may cause reduction of $Ni^{2+}$ to $Ni^{+}$ and $Ni^{0}$. The pre-reduction of hydrogenating metal ions to an oxidation state of between +1 and 0 was useful in retarding the coke formation during the alkylation reactions, and thus increasing the catalyst stability.

After pretreatment, the catalyst may be contacted with an appropriate feed under alkylation reaction conditions to carry out the aromatic alkylation. Examples of alkylation reactions for which the invention has application include toluene alkylation with an alkylating agent such as methanol. Other examples may include gas phase toluene disproportionation in the presence of hydrogen producing benzene and mixed xylenes.

While the invention has application to many aromatic alkylation reactions, it is particularly well suited for toluene methylation using ZSM-5-type zeolite catalysts. The ZSM-5 catalyst may or may not possess shape selective properties. Although much of the description herein may be directed to such toluene methylation, it will be readily understood by those skilled in the art that it is not solely limited to such.

As used herein, the expression "ZSM-5-type" is meant to refer to those zeolites that are isostructurally the same as ZSM-5 zeolites. Additionally, the expressions "ZSM-5" and "ZSM-5-type" may also be used herein interchangeably to encompass one another and should not be construed in a limiting sense. The ZSM-5 zeolite catalysts and their preparation are described in U.S. Pat. No. 3,702,886, which is herein incorporated by reference. In the present invention, the ZSM-5 zeolite catalyst may include those having a $SiO_2/Al_2O_3$ molar ratio of from 10 to 1000, more particularly from about 30 to about 500. The ZSM-5 catalyst is a medium pore-size zeolite with a pore diameter of from about 5.1 to about 5.6 Å.

As used herein, catalytic activity can be expressed as the % moles of toluene converted with respect to the moles of toluene fed and can be defined as:

$$\text{Mole \% Toluene Conversion} = [(T_i - T_o)/T_i] \times 100 \quad (2)$$

where, $T_i$ is the number of moles of toluene fed and $T_o$ is the number of moles toluene unreacted. As used herein, selectivity for total xylenes may be expressed as:

$$\text{Mole \% Total Xylene Selectivity} = [(X_{tx}/(T_i - T_o)] \times 100 \quad (3)$$

where, $X_{tx}$ is the number of moles of total (o-, m- or p-) xylenes in the product.

The reactor pressure for toluene methylation or other aromatic alkylation may vary, but typically ranges from about 10 to about 1000 psig.

The reaction may be carried in a variety of different reactors that are commonly used for carrying out aromatic alkylation reactions. Single or multi reactors in series and/or parallel are suitable for carrying out the toluene methylation or other aromatic alkylation reactions.

The following examples better serve to illustrate the invention.

EXAMPLES

Catalyst Preparation

Catalyst A

The starting material was an $NH_4$-ZSM-5 zeolite powder having a $SiO_2/Al_2O_3$ mole ratio of 80. Ni was added in the zeolite by an ion-exchange procedure. The nickel salt used for the ion exchange of ZSM-5 was nickel (II) nitrate hexahydrate. In the ion-exchange procedure, 2.91 g of nickel (II) nitrate hexahydrate was dissolved in 200 ml of deionized water. About 60 g of $NH_4$-ZSM-5 zeolite powder was added to 500 ml of deionized water in a beaker and was made into zeolite slurry by stirring using a magnetic stirrer. This slurry was heated to approximately 90° C. To this zeolite slurry, the nickel salt solution was added and the ion-exchange was continued for 3–4 hours. Under these conditions, a nickel loading of 1 wt. % of the zeolite is expected. After the ion exchange, the zeolite was filtered, washed with deionized water and dried at 90° C. overnight. The zeolite powder was then bound with alumina (20% by weight) to form the catalyst and the catalyst was calcined at 530° C. in air for 10 h and was sized between 20 and 40 mesh.

Catalyst B

The starting material was an $NH_4$-ZSM-5 zeolite powder having a $SiO_2/Al_2O_3$ mole ratio of 280. A hydrogenating metal, nickel, was impregnated in the zeolite by using the following method: For 1.0 wt % Ni loading, 1.47 g nickel salt, nickel (II) nitrate hexahydrate, was dissolved in 100 ml of deionized water. About 30 g of $NH_4$-ZSM-5 zeolite powder was added to 400 ml of deionized water in a beaker and was made into zeolite slurry by stirring using a magnetic stirrer. The Ni-salt solution was then added to the zeolite slurry and heated to evaporate all liquid, and the zeolite was then dried at 90° C. overnight. The Ni-impregnated zeolite powder was then bound with a lumina as a binder (20% by wt.) to form the catalyst. The catalyst was then calcined at temperature of 530° C. for 10 hours and was sized to between 20 and 40 mesh.

Catalyst C

The starting material was an $NH_4$-ZSM-5 zeolite powder having a $SiO_2/Al_2O_3$ mole ratio of 280. A hydrogenating metal as nickel was impregnated on the zeolite using the following method: For 1.5 wt % Ni loading, 2.24 g nickel salt, nickel (II) nitrate hexahydrate, was dissolved in 100 ml of deionized water. About 30 g of $NH_4$-ZSM-5 zeolite powder was added to 400 ml of deionized water in a beaker and was made into a zeolite slurry by stirring using a magnetic stirrer. The Ni-salt solution was then added to the zeolite slurry and heated to evaporate all liquid, and the zeolite was then dried at 90° C. overnight. The Ni-impregnated zeolite powder was then bound with a lumina as a binder (20% by wt.) to form the catalyst. The catalyst was then calcined at temperature of 530° C. for 10 hours and was sized to between 20 and 40 mesh.

Catalyst D

The starting material was an NH$_4$-ZSM-5 zeolite powder having a SiO$_2$/Al$_2$O$_3$ mole ratio of 280. The NH$_4$-ZSM-5 zeolite powder was bound with alumina as a binder (20% by wt.) to form the catalyst. The catalyst was then calcined at temperature of 530° C. for 10 hours and was sized to between 20 and 40 mesh.

Hereafter, catalysts A through C containing Ni either ion-exchanged or impregnated in NH$_4$-ZSM-5, bound with alumina, and calcined will be termed as Ni-HZSM-5. Similarly, catalysts D will be termed as HZSM-5.

Example 1

A Ni-HZSM-5 zeolite catalyst (catalyst A) was used in this example. About 2.9 ml of catalyst A was loaded into a fixed, continuous flow type reactor. The catalyst was dried by slowly raising the catalyst bed temperature (about 5° C./min) to 150° C. under hydrogen (H$_2$) flow for one hour. The catalyst was further treated by slowly increasing (ramp rate of about 3° C./min) the catalyst bed temperature to 350° C. under hydrogen flow for about 3 hr. Premixed toluene and methanol feed (molar ratio 2.0) was added to the reactor at 350° C. and maintained a liquid hourly space velocity (LHSV) about 1.5 hr$^{-1}$ and cofeed of H$_2$ gas was fed and maintained to provide a H$_2$/HC molar ratio of about 2.0 (where HC=toluene+methanol). The reactor pressure was 20 psig. Catalyst bed inlet temperature was raised to obtain an initial toluene conversion of around 30%, which was maintained by adjusting the catalyst bed temperature. The results are presented in Table 1 below and in FIG. 1.

TABLE 1

| Time on Stream, hr | Bed Inlet Temp, ° C. | Toluene Conv (%) |
|---|---|---|
| 3.3 | 455 | 24.4 |
| 4.3 | 450 | 29.8 |
| 21.3 | 454 | 33.6 |
| 27.8 | 455 | 34.3 |
| 45.3 | 460 | 34.7 |
| 51.8 | 463 | 33.9 |
| 69.3 | 460 | 33.9 |
| 75.8 | 468 | 34.0 |
| 92.8 | 471 | 32.1 |
| 99.8 | 475 | 30.8 |

As shown in Table 1 and in FIG. 1, about 30% toluene conversion was obtained at about 450° C. To maintain the constant conversion level the reactor temperature was adjusted at rate of about 0.2° C./hour, which correlates to catalyst deactivation rate.

Example 2

As in Example 1, catalyst A was used. The catalyst was pretreated differently, however, prior to feed introduction. A fresh load of catalyst A (5.4 ml) was loaded into a fixed, continuous flow type reactor. The catalyst was dried by slowly raising the catalyst bed temperature (about 5° C./min) to 150° C. under hydrogen (H$_2$) flow for one hour. The catalyst was further treated by slowly (ramp rate of about 3° C./min) increasing the catalyst bed temperature to 430° C. under hydrogen flow for about 3 hr. Toluene and methanol premixed feed (molar ratio 2/1) was added to the reactor after lowering the catalyst bed temperature to 350° C. The liquid hourly space velocity (LHSV) was maintained at about 1.6 hr$^{-1}$ and cofeed H$_2$ gas was fed to maintain a H$_2$/HC molar ratio of about 2.0. The reactor pressure was 20 psig. The catalyst bed temperature was raised to about 450° C. Under these conditions toluene conversion was about 30%. The results are presented in Table 2 below and in FIG. 1.

TABLE 2

| Time on Stream, hr | Bed Inlet Temp, ° C. | Toluene Conv (%) |
|---|---|---|
| 16.8 | 355 | 27.5 |
| 23.3 | 363 | 29.7 |
| 40.8 | 364 | 30.0 |
| 47.3 | 381 | 32.0 |
| 64.8 | 378 | 33.1 |
| 71.3 | 379 | 32.3 |
| 88.8 | 378 | 32.3 |
| 94.8 | 383 | 31.5 |
| 160.8 | 376 | 31.2 |
| 191.3 | 381 | 29.7 |

By comparing initial activity or toluene conversions from Examples 1 and 2, it appears that about the same toluene conversion was obtained at 60–80° C. lower when pretreating the catalyst A at 430° C. instead of at 350° C., as described above. Obtaining the same conversion at a lower temperature reflects an increased catalyst activity. That is, in Example 2, a 60–80° C. higher initial activity was obtained for the catalyst treated at 350° C. compared to the pretreated catalyst A at 430° C., as described above. After an initial period, a stable toluene conversion was maintained without requiring a reactor temperature increase, at least for 190 hours shown in Example 2.

Example 3

A Ni-HZSM-5 zeolite catalyst (catalyst B) was tested after pretreating with H$_2$ at 430° C. A fresh load (4.9 ml) of catalyst B was loaded into a fixed, continuous flow type reactor. The catalyst was dried by slowly raising the catalyst bed temperature (about 5° C./min) to 150° C. under hydrogen (H$_2$) flow for one hour. The catalyst was further treated by slowly increasing the catalyst bed temperature (ramp rate of about 2° C./min) to 430° C. under hydrogen flow for about 3 hr. Toluene and methanol premixed feed (molar ratio 3/1) was added to the reactor after lowering the reactor temperature to 300° C. A liquid hourly space velocity (LHSV) of about 2.0 hr$^{-1}$ was maintained and a cofeed H$_2$ gas was fed and maintained to provide a H$_2$/HC molar ratio of about 1.9. The reactor pressure was about 20 psig. The catalyst bed temperature was slowly raised to about 430° C. Under these conditions toluene conversion was about 20%. The results are presented in Table 3 below and in FIG. 2.

TABLE 3

| Time on Stream, hr | Bed Inlet Temp, ° C. | Toluene Conv (%) |
|---|---|---|
| 7.5 | 356 | 12.8 |
| 24.0 | 356 | 13.5 |
| 30.5 | 389 | 14.3 |
| 48.5 | 391 | 14.9 |
| 55.5 | 432 | 16.6 |
| 120.0 | 432 | 18.1 |
| 127.5 | 433 | 19.4 |
| 144.0 | 432 | 19.4 |
| 151.5 | 434 | 19.5 |
| 168.0 | 433 | 19.7 |
| 175.5 | 434 | 19.7 |

TABLE 3-continued

| Time on Stream, hr | Bed Inlet Temp, °C. | Toluene Conv (%) |
|---|---|---|
| 192.0 | 432 | 20.0 |
| 199.5 | 431 | 20.5 |
| 288.0 | 432 | 19.5 |
| 295.5 | 433 | 20.3 |
| 312.0 | 431 | 21.1 |
| 336.5 | 433 | 19.9 |
| 360.0 | 431 | 19.8 |
| 384.0 | 430 | 20.5 |
| 390.5 | 430 | 20.6 |
| 457.0* | 434 | 21.0 |
| 463.5 | 431 | 21.6 |
| 487.5 | 434 | 21.2 |
| 511.5 | 430 | 19.6 |
| 535.5 | 429 | 21.1 |
| 625.0 | 430 | 20.5 |
| 649.5 | 430 | 19.9 |
| 672.5 | 431 | 19.7 |
| 696.5 | 433 | 19.7 |
| 816.5* | 431 | 19.9 |
| 840.0 | 429 | 19.1 |
| 865.0 | 430 | 19.7 |
| 895.5 | 431 | 18.8 |
| 960.5 | 431 | 17.1 |
| 929.4 | 429 | 13.9 |
| 984.5 | 432 | 12.6 |
| 988.2 | 429 | 12.4 |

*Continuous run interrupted due to power outage; data collected after restart.

Figure 2:
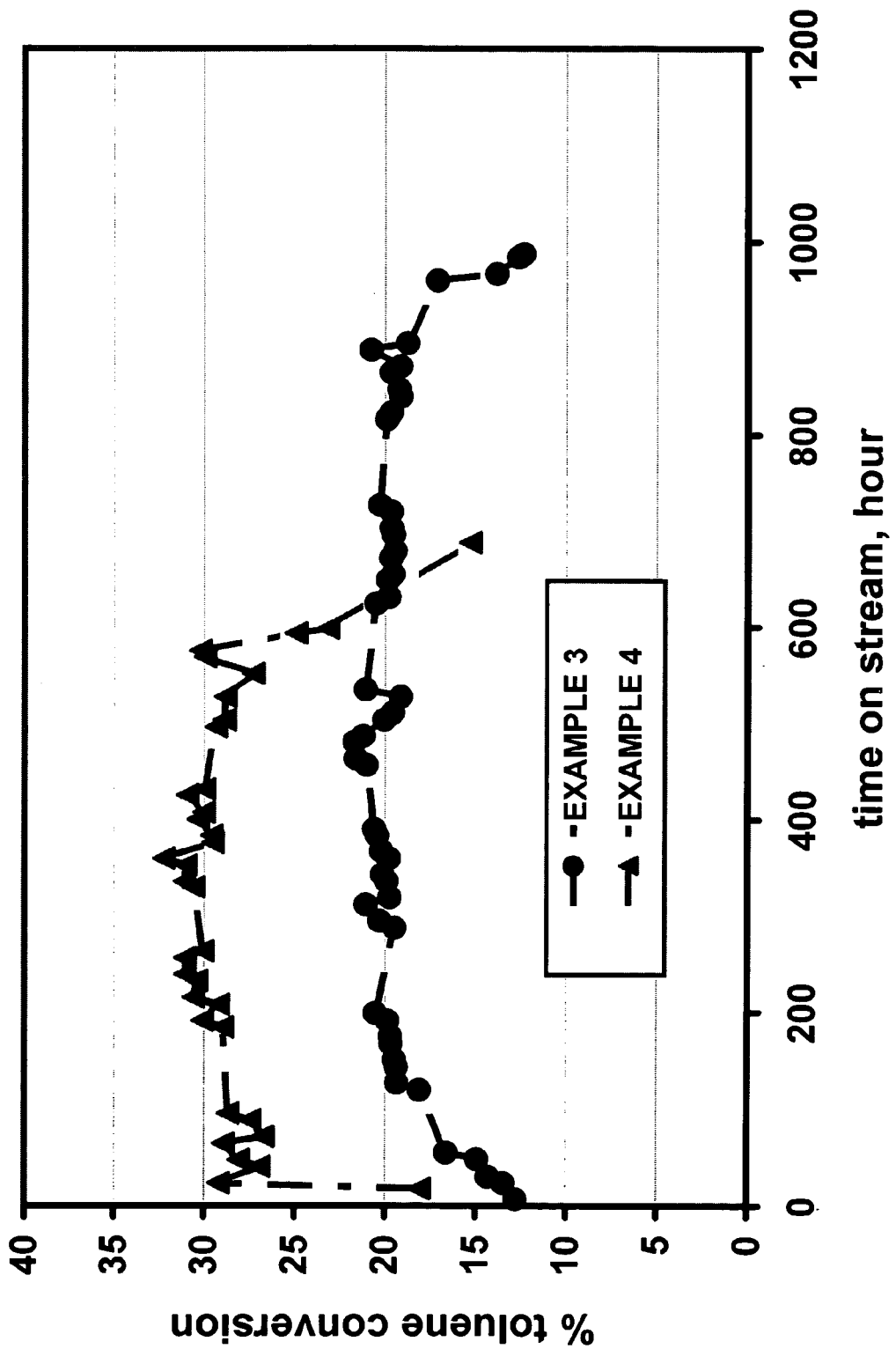
FIG. 2 is a plot of toluene conversion over time for the toluene methylation reactions of Examples 3 and 4.

Data shown in Table 3 and FIG. 2, a stable toluene conversion (about 20%) was maintained without requiring reactor temperature increase for nearly 1000 hour.

Example 4

A Ni-HZSM-5 zeolite catalyst (catalyst B) was used in this example. The catalyst pretreatment and start-up conditions used in examples 3 and 4 were almost the same, except the toluene methanol ratios were different. A fresh load of catalyst B (7.2 ml) was loaded into fixed, continuous flow type reactor. The catalyst was dried by slowly raising the catalyst bed temperature (about 5° C./min) to 150° C. under hydrogen ($H_2$) flow for one hour. The catalyst was further treated by slowly (ramp rate of about 3° C./min) increasing the catalyst bed temperature to 430° C. under hydrogen flow for about 3 hr. Toluene and methanol premixed feed (molar ratio 2/1) was added to the reactor. A liquid hourly space velocity (LHSV) of about 2.0 $hr^{-1}$ was maintained and cofeed $H_2$ gas was fed and maintained at a $H_2$/HC molar ratio of about 1.8. The reactor pressure was about 20 psig. The catalyst bed temperature was raised to about 430° C. Under these conditions toluene conversion was about 30%. The results are presented in Table 4 below and in FIGS. 2 and 4. As shown in Table 4 and FIG. 2, the catalyst appeared to show stabile toluene conversion during the run for up to about 600 hours.

TABLE 4

| Time on Stream, hr | Bed Inlet Temp, °C. | Toluene Conv (%) |
|---|---|---|
| 17.8 | 433 | 18.1 |
| 23.8 | 436 | 29.2 |
| 40.8 | 434 | 26.9 |
| 64.8 | 430 | 28.9 |
| 71.8 | 437 | 26.7 |
| 88.8 | 436 | 27.4 |
| 95.8 | 432 | 28.7 |
| 184.8 | 431 | 29.0 |

TABLE 4-continued

| Time on Stream, hr | Bed Inlet Temp, °C. | Toluene Conv (%) |
|---|---|---|
| 191.8 | 434 | 30.1 |
| 208.3 | 430 | 29.2 |
| 215.8 | 429 | 30.6 |
| 233.3 | 430 | 30.4 |
| 239.8 | 435 | 31.0 |
| 256.8 | 432 | 31.0 |
| 263.8 | 430 | 30.1 |
| 329.8 | 429 | 30.6 |
| 335.8 | 429 | 31.1 |
| 352.8 | 431 | 31.0 |
| 359.8 | 428 | 32.2 |
| 376.3 | 428 | 29.5 |
| 383.8 | 431 | 29.6 |
| 400.3 | 431 | 30.3 |
| 407.8 | 429 | 30.0 |
| 425.8 | 429 | 30.9 |
| 496.8 | 430 | 30.0 |
| 503.8 | 431 | 28.9 |
| 551.8 | 429 | 27.3 |
| 569.3 | 431 | 29.9 |
| 575.8 | 428 | 30.2 |
| 593.8 | 430 | 25.0 |
| 598.8 | 429 | 23.2 |
| 688.3 | 430 | 15.3 |

Example 5

Figure 3:
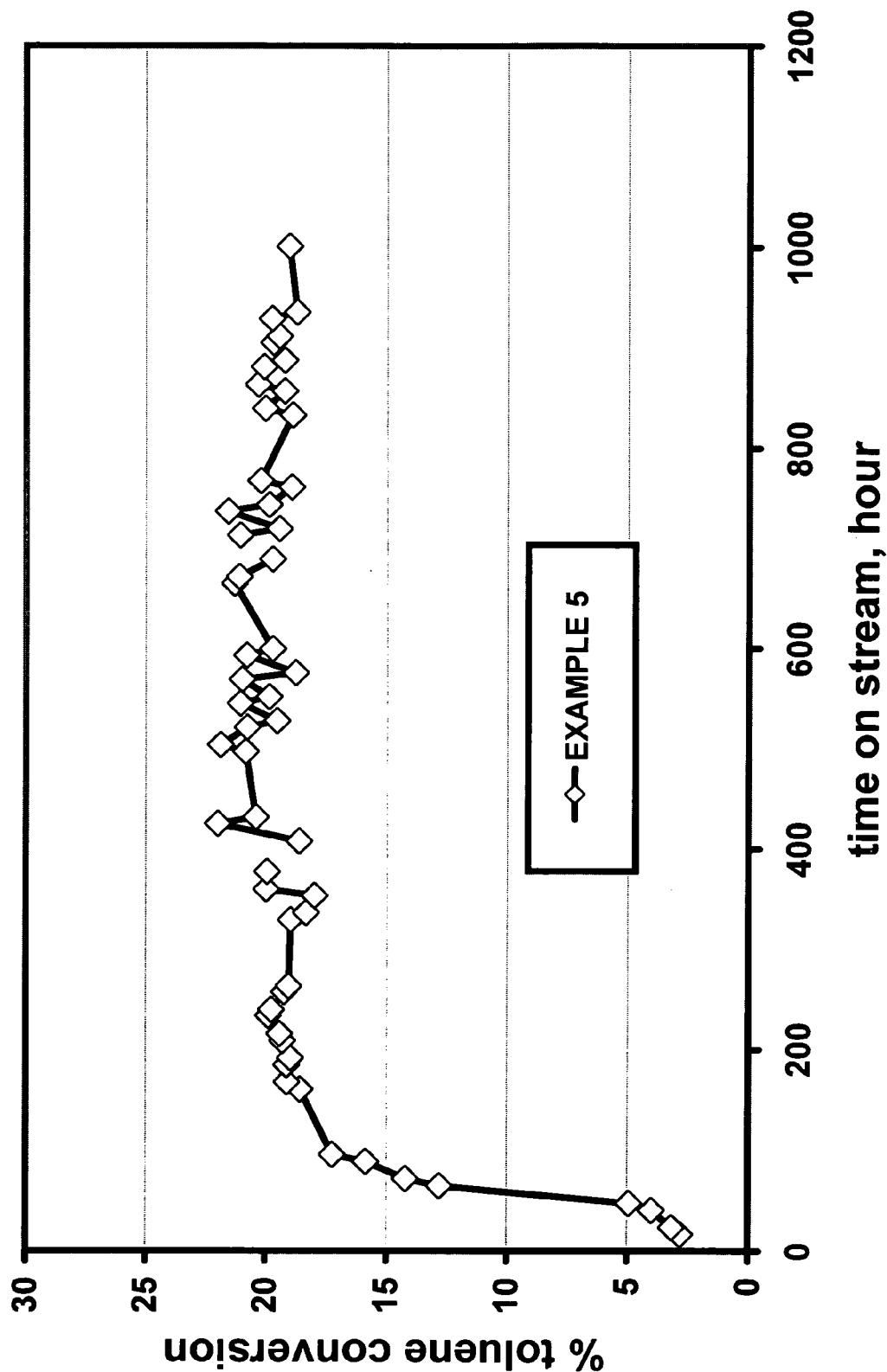
FIG. 3 is a plot of toluene conversion over time for the toluene methylation reactions of Example 5.

A Ni-HZSM-5 zeolite catalyst (catalyst C) was tested after pretreating with $H_2$ at 430° C. A fresh load of catalyst C (6.0 ml) was loaded into a fixed, continuous flow type reactor. The catalyst was dried in each case by slowly raising the catalyst bed temperature (about 5° C./min) to 150° C. under hydrogen ($H_2$) flow for one hour. The catalyst was further treated by slowly (ramp rate of about 2° C./min) increasing the catalyst bed temperature to 430° C. under hydrogen flow for about 3 hr. Toluene and methanol premixed feed (molar ratio 3/1) was added to reactor after lowering the catalyst bed temperature to 350° C. A liquid hourly space velocity (LHSV) about 2.0 $hr^{-1}$ was maintained and a cofeed of $H_2$ gas was fed into the reactor to maintain a $H_2$/HC molar ratio of about 2.0. The reactor pressure was 20 psig. The catalyst bed temperature was raised slowly to around 430° C. Under these conditions toluene conversion was about 20%. The results are presented in Table 5 below and in FIG. 3. As shown in Table 5 and FIG. 3, the catalyst appeared to show stable toluene conversion for about 1000 hours.

TABLE 5

| Time on Stream, hr | Bed Inlet Temp, °C. | Toluene Conv (%) |
|---|---|---|
| 16.4 | 349 | 2.8 |
| 40.4 | 381 | 4.0 |
| 64.4 | 406 | 12.8 |
| 71.4 | 408 | 14.2 |
| 88.4 | 419 | 15.9 |
| 95.4 | 431 | 17.2 |
| 160.4 | 429 | 18.6 |
| 184.4 | 430 | 19.1 |
| 208.4 | 429 | 19.3 |
| 233.4 | 431 | 19.9 |
| 256.9 | 429 | 19.2 |
| 328.9 | 431 | 19.0 |
| 376.9 | 430 | 20.0 |
| 407.4 | 428 | 18.6 |
| 431.4 | 433 | 20.4 |
| 496.9 | 427 | 20.8 |

TABLE 5-continued

| Time on Stream, hr | Bed Inlet Temp, ° C. | Toluene Conv (%) |
|---|---|---|
| 520.9 | 428 | 20.8 |
| 544.9 | 428 | 21.1 |
| 568.9 | 427 | 21.0 |
| 592.9 | 428 | 20.8 |
| 664.9 | 427 | 21.3 |
| 688.9 | 428 | 19.7 |
| 712.9 | 428 | 21.1 |
| 760.9 | 430 | 18.9 |
| 832.9 | 428 | 18.9 |
| 887.4 | 432 | 19.2 |
| 911.4 | 432 | 19.4 |
| 935.0 | 429 | 18.7 |
| 1000.9 | 429 | 19.0 |
| 1007.9* | 434 | 14.3 |
| 1025.4 | 430 | 10.2 |
| 1048.9 | 428 | 9.8 |

*Reactor lost toluene/methanol feed

Comparative Example 6

For comparison, a HZSM-5 catalyst (catalyst D) was tested. A fresh load of catalyst D (3.1 ml) was loaded into a fixed, continuous flow type reactor. The catalyst was dried in each case by slowly raising the catalyst bed temperature (about 5° C./min) to 350° C. under hydrogen ($H_2$) flow for at least 1 h prior to feed introduction. Toluene and methanol premixed feed (molar ratio 2/1) was added to the reactor after lowering the catalyst bed temperature to 300° C., and maintained a liquid hourly space velocity (LHSV) of about 1.5 hr$^{-1}$ and a cofeed of $H_2$ gas was fed to maintain a $H_2$/HC molar ratio of about 2.0. The reactor pressure was about 20 psig. The catalyst bed temperature was raised to about 450° C. Under these conditions toluene conversion was about 30%. The results are presented in Table 6 below and in FIG. 4.

TABLE 6

| Time on stream/hr | Bed Inlet Temp/° C. | Toluene Conv., % |
|---|---|---|
| 2.5 | 453 | 31.0 |
| 3.5 | 450 | 31.0 |
| 20.0 | 454 | 30.7 |
| 26.5 | 451 | 31.8 |
| 44.0 | 450 | 31.4 |
| 50.5 | 452 | 32.3 |
| 68.0 | 452 | 31.7 |
| 74.5 | 451 | 31.5 |
| 92.0 | 450 | 31.3 |
| 98.0 | 457 | 30.9 |
| 164.0 | 450 | 31.1 |
| 170.5 | 455 | 30.7 |
| 188.0 | 449 | 31.1 |
| 194.5 | 449 | 30.0 |
| 212.0 | 452 | 29.0 |
| 218.5 | 457 | 28.3 |

Figure 4:
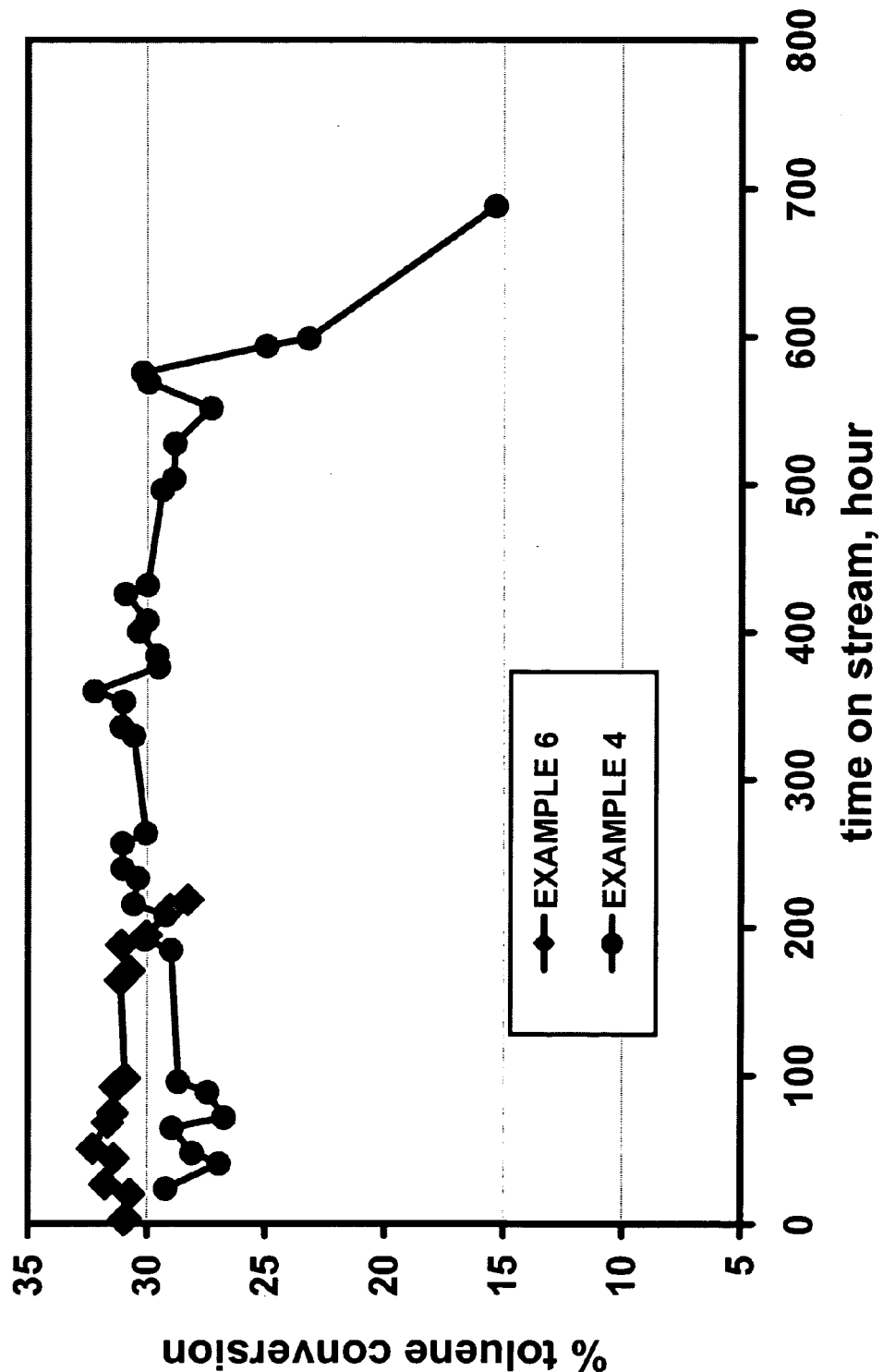
FIG. 4 is a plot of toluene conversion over time for the toluene methylation reactions of Examples 6 and 4.

As shown in FIG. 4, the HZSM-5 catalyst started deactivating after about 200 hours, showing decreasing toluene conversion. In contrast, the Ni-modified catalyst of Example 4 showed significantly increased catalyst stability, maintaining stable toluene conversion for about 600 hours.

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

We claim:

1. An aromatic alkylation catalyst for use in aromatic alkylazion comprising:
   a zeolite having a silica/alumina molar ratio of greater than 200 with a pore size of from about 5.0 to about 7.0 Å containing a hydrogenating metal in an amount of from 0.1% to about 5.0% by total weight of catalyst.

2. A method of treating a zeolite catalyst for use in aromatic alkylation to increase catalyst stability comprising:
   providing a zeolite catalyst having a silica/alumina molar ratio of greater than 200 with a pore size about 5.0 to 7.0 Å;
   treating the medium pore zeolite catalyst with a hydrogenating metal; and
   heating the hydrogenating metal-treated zeolite catalyst in the presence of a reducing agent prior to use in an aromatic alkylation reaction to a temperature of from about 400° C. to about 500° C. for about 0.5 to about 10 hours.

3. The method of claim 2, wherein:
   the zeolite catalyst is a ZSM-5 type catalyst.

4. The method of claim 2, wherein:
   the hydrogenating metal-treated catalyst is heated to a temperature of from about 410° C. to about 450° C.

5. The method of claim 2, wherein:
   the hydrogenating metal is selected from the group consisting of nickel, palladium and platinum.

6. The method of claim 2, wherein:
   the reducing agent is hydrogen gas.

7. A catalyst for use in aromatic alkylation comprising:
   a zeolite having a silica/alumina molar ratio of greater than 200 with a pore size of from about 5.0 to about 7.0 Å containing a hydrogenating metal of nickel in an amount of from 0.1 to about 5.0 by total weight of catalyst.

8. The catalyst of claim 1, wherein:
   the hydrogenating metal is a group VIIIA metal.

9. The catalyst of claim 1, wherein:
   the hydrogenating metal is selected from a group consisting of nickel, palladium and platinum.

10. The catalyst of claim 1, wherein:
    the zeolite catalyst is a ZSM-5-type zeolite catalyst.

11. The method of claim 2, wherein:
    the hydrogenating metal is a group VIIIA metal.

12. The catalyst of claim 7, wherein:
    the zeolite catalyst is a ZSM-5 type catalyst.

13. The method of claim 2, wherein:
    the hydrogenating metal-treated catalyst is heated to a temperature of from about 410° C. to about 450° C.

14. The method of claim 2, wherein:
    the reducing agent is hydrogen gas.

15. The catalyst of claim 1, wherein:
    the catalyst contains no rare-earth ion stabilizing component.

16. The method of claim 2, wherein:
    the catalyst is not treated with any rare-earth ion stabilizing component.

17. The catalyst of claim 7, wherein:
    the catalyst contains no rare-earth ion stabilizing component.

* * * * *